US00RE37209E

(19) United States
(12) Reissued Patent
Hensley et al.

(10) Patent Number: US RE37,209 E
(45) Date of Reissued Patent: Jun. 5, 2001

(54) EXTENSION DECELERATION ORTHOSIS

(76) Inventors: David Ellis Hensley; Bradley Russell Kielman, both of c/o Greater Seattle Prosthetic and Orthotic Center, Inc., 609 Market St., Kirland, WA (US) 98033

(21) Appl. No.: 08/406,772

(22) Filed: Mar. 16, 1995

Related U.S. Patent Documents

Reissue of:
(64) Patent No.: 4,865,024
Issued: Sep. 12, 1989
Appl. No.: 07/260,943
Filed: Oct. 21, 1988

U.S. Applications:

(63) Continuation of application No. 08/243,554, filed on May 16, 1994, now abandoned, which is a continuation-in-part of application No. 07/959,452, filed on Oct. 8, 1992, now abandoned, which is a continuation of application No. 07/444,782, filed on Dec. 1, 1989, now abandoned.

(51) Int. Cl.[7] ..... A61F 5/01
(52) U.S. Cl. ..... 602/26
(58) Field of Search ..... 602/5, 6, 23, 26–28

(56) References Cited

U.S. PATENT DOCUMENTS

| | | |
|---|---|---|
| 817,785 | 4/1906 | Kritsch . |
| 1,072,369 | 9/1913 | Spahn . |
| 4,320,747 | 3/1982 | Daniell, Jr. . |
| 4,337,764 | 7/1982 | Lerman . |
| 4,361,142 | 11/1982 | Lewis et al. . |
| 4,370,977 | 2/1983 | Mauldin et al. . |
| 4,372,298 | 2/1983 | Lerman . |
| 4,428,369 | 1/1984 | Peckham et al. . |
| 4,433,679 | 2/1984 | Mauldin et al. . |
| 4,487,200 | 12/1984 | Feanny et al. . |
| 4,489,718 | 12/1984 | Martin . |
| 4,503,846 | 3/1985 | Martin . |
| 4,506,661 | 3/1985 | Foster . |
| 4,524,764 | 6/1985 | Miller et al. . |
| 4,751,920 | 6/1988 | Mauldin et al. . |
| 4,803,975 | 2/1989 | Meyers . |

FOREIGN PATENT DOCUMENTS

| | | |
|---|---|---|
| 304059 | 1/1982 | (DE) . |
| 2098490 | 11/1982 | (GB) . |
| 37574 | 8/1956 | (PL) . |
| 8400264 | 6/1985 | (WO) . |

*Primary Examiner*—Michael Peffley
(74) *Attorney, Agent, or Firm*—Richard D. Multer

(57) ABSTRACT

An extension deceleration orthotic fulcrum for knee and elbow braces, which simulates performance of the function of those ligaments that control joint motion and [provide] *provides* anteroposterior joint stability, comprising a lightweight, external spring assembly, upper and lower elongated arms, and a centric or polycentric fulcrum, which is adjustable for its range of motion, adaptable for use on many different style orthoses, and whose strength can be varied to suit corrective, preventive, anthropomorphic, environmental, and usage requirements, including means both for mechanically dampening the limb's angular velocity on extension to prevent hyperextension and for accelerating the limb's angular velocity on flexion to enable quicker, smoother, less stressful motion. In one embodiment spring rods are assembled medially and laterally to conventional pairs of elongated orthotic brace arms to span the joint fulcrum point by serpentinely engaging novel roller posts, the assemblage thus serving to decelerate the limb during the last 15 to 20 degrees of extension, to help prevent the striking of a stop with its attendant risk of hyperextension, and thus serving to use the stored energy of the spring to facilitate flexion of the limb.

11 Claims, 3 Drawing Sheets

EXTENSION DECELERATION ORTHOSIS

Matter enclosed in heavy brackets [ ] appears in the original patent but forms no part of this reissue specification; matter printed in italics indicates the additions made by reissue.

*This application is a continuation of U.S. Ser. No. 08/243,554 filed May 16, 1994 (now abandoned), which is a reissue of U.S. Ser. No. 08/099,249 filed Jul. 29, 1993 (now abandoned), which is a continuation of U.S. Ser. No. 07/959, 452 filed Oct. 8, 1992 (now abandoned), which is a continuation of U.S. Ser. No. 07/444,782 filed Dec. 1, 1989 (now abandoned), which is a reissue of U.S. Ser. No. 07/260,943 filed Oct. 21, 1988 and issued as U.S. Pat. No. 4,865,024.*

FIELD OF THE INVENTION

This invention relates to [orthosis] *orthoses* for the prevention or rehabilitation of joint injuries. It relates to an orthotic fulcrum, and for point design particularly to decelerate in one direction eliminating instability and motion problems with respect to joint extension, hyperextension, or flexion.

DESCRIPTION OF THE PRIOR ART

Just as there are many indications for orthotic management of knee and elbow joints so are there many varieties of braces for the leg and arm. Joint extension in physically active individuals, such as athletes, or in people having joint injuries, can introduce instability and the risk of injury or further injury due to the increased angular limb velocities associated with their activities or relative to their disability. Joint flexion in these people can also place severe energy and fatigue costs on their quadriceps or triceps muscles. While prior art braces include desirable features for providing extension stability, for limiting hyperextension and for providing flexion mobility, they have the kinds of problems described below.

Means for limiting hyperextension, such as pins abuting edges, co-engaging recesses and shoulders, and stops near the fulcrum to limit angular motion, themselves provide the fulcrum about which accelerating and extending limbs can rotate into injurious hyperextension. In other words, the braces themselves can do harm. Free motion braces have similar problems. Friction control arrangements, while slowing limb extension, have the disadvantage of requiring force to overcome the designed-in friction forces when the limb is flexed, a disadvantage to athletes needing quick reaction and to patients needing to conserve energy stores and avoid undue fatigue. Also, stops, pins, edges, shoulders and like tend to add undesirable weight to a brace, increasing fatigue, slowing motion, and adding discomfort. Finally, the kinds of features described in *the* prior art for extension/flexion stability/mobility generally are uniquely built into the knee or elbow brace design and are thus neither economically adaptable to a wide variety of other braces nor easily adjustable to wearer, medical or athletic needs.

The foregoing problems suggest the following minimal design criteria for an orthotic device providing extension stability, limiting hyperextension, and providing flexion mobility:

1. Should automatically decelerate the angular velocity of the limb during the last fifteen to twenty degrees of design motion prior to contact with any stop, pin, shoulder or similar stopping means.

2. Should not slow the speed of ranging of the joint other than as specified in 1 above.

3. Should be lightweight.

4. Should be economically adaptable to a wide range of braces.

5. Should be economical of manufacture and assembly.

6. Should be adjustable with respect to the range of motion within which it operates.

7. Should be adjustable with respect to the forces expected to be encountered by the limb, as conditioned by the user's activity level, state of health, weight, and usage environment, e.g., playing surface as in the case of athletics.

SUMMARY OF THE INVENTION

It is the object of this invention to meet the foregoing design requirements with features which solve the problems heretofore described, which also renders it a vast improvement on [it's] *its* original merits over *the* prior art.

An orthotic device with a particularly designed fulcrum point which limits hyperextension, provides extension stability, and facilitates flexion mobility is provided. The device includes adjustable and adaptable spring rods attached near brace fulcrum points(s) with a novel post and pivot arrangement, as depicted in the drawings. As the hinge is rotated toward the fully extended position, i.e., so that the arms form an angle of 180 degrees with each other, twin posts engage the spring rods to cause deceleration of the angular motion.

One embodiment includes conventional upper and lower rigid elongated arms with geared ends and integral [stop] *stops* for limiting rotation beyond 180 degrees, together with means for linking the arms adjacently and for rotating the arms in the same plane about a pivot or pivot points. An assembly of plates, spacers, bushings and screws is provided to secure the arms and to insure they rotate in the same plane. The assembly is designed both to permit the arms to be locked in any position during manufacture, while fitting the orthotic fulcrum assembly to an orthosis, and also to permit free motion of the arms during usage so that the speed of motion of the ranging of the joint is not reduced or impaired. In one embodiment a lightweight spring rod is serpentinely assembled to the orthotic fulcrum's *outer* connecting plate by means of friction reduction roller posts and central pivot screw. Placement of the roller posts controls the point during limb extension when the spring rod is activated, with roller post positioning being determined during manufacture by the needs of the user with respect to limitation of the range of motion, *the* point at which deceleration of limb angular motion is required and the like. Since the spring rod mechanically dampens the rate of angular motion of the hinge, adjustment of the rate of deceleration is controlled by adjusting the material or cross-sectional area of the spring rod to change the force required. Adjustment of the point at which deceleration starts is controlled by the variable placement of the roller posts so as to engage the spring rod sooner or later during the extension process. As shown in the drawings, the spring assembly can be easily adapted to a variety of different hinges and braces.

These and other features and benefits of this invention will be obvious from the drawings and disclosure which follow.

*BRIEF DESCRIPTION OF THE* DRAWINGS

DETAILED DESCRIPTION *OF THE INVENTION*

Figure 1:
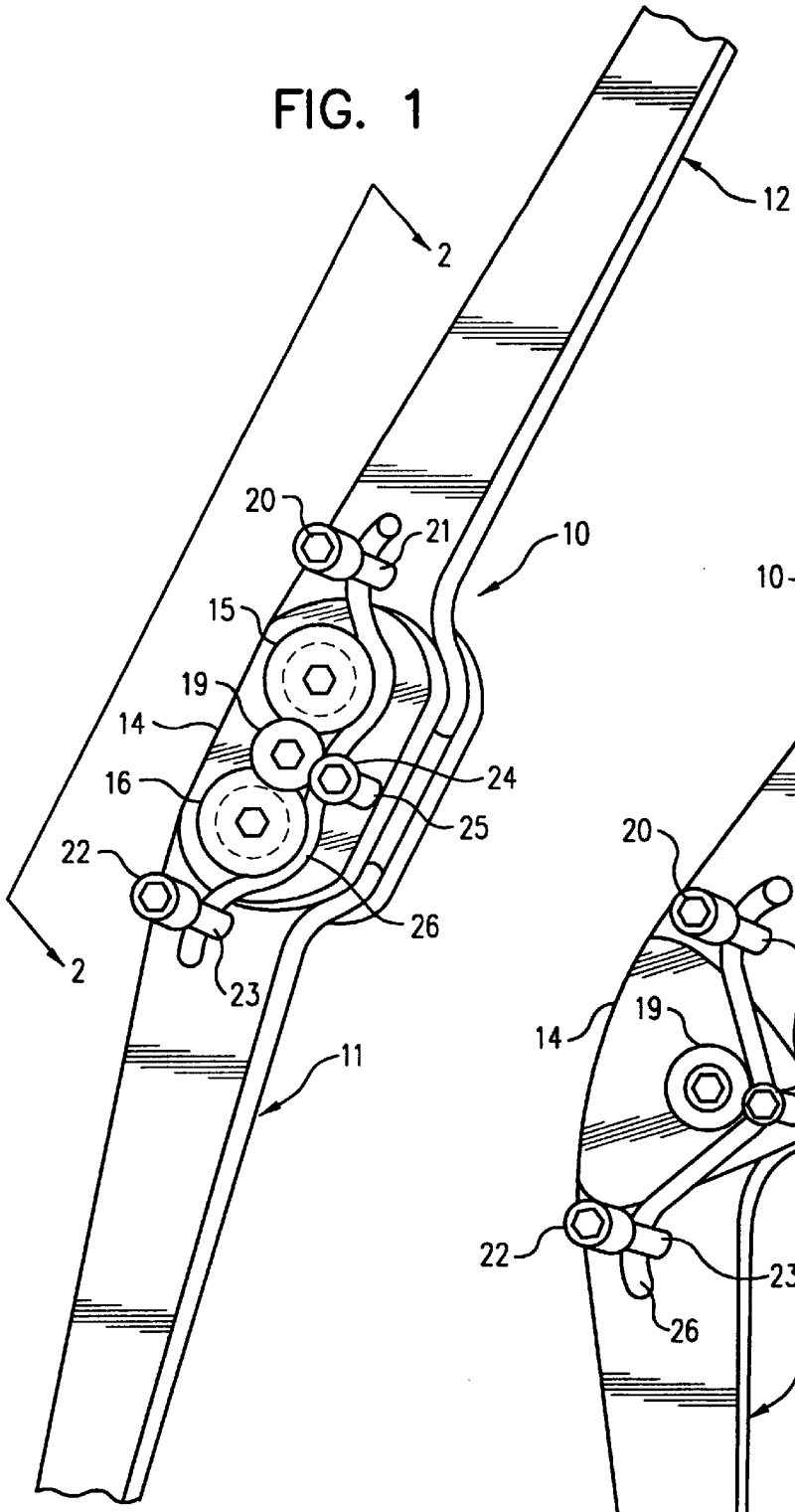
FIG. 1 is a perspective view of an extension deceleration orthotic hinge according to *the* principles of this invention[:]*;*
Figure 4:
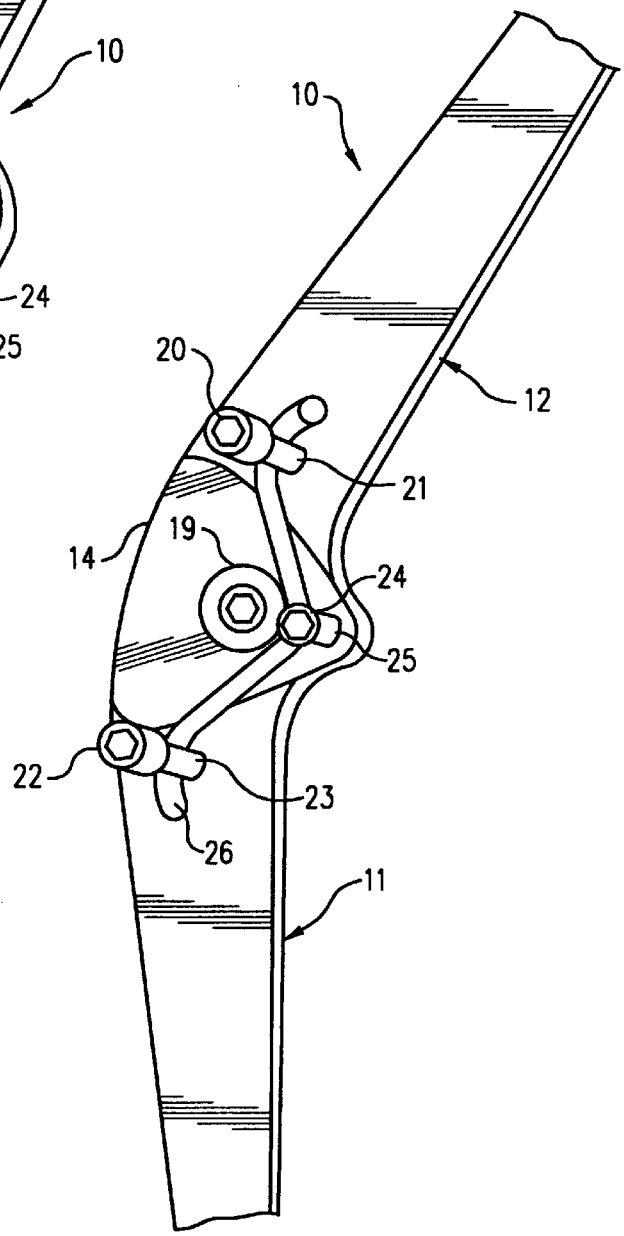
FIG. 4 is a fragmentary perspective view showing how the spring rod, roller posts, and pivot screw assembly [is] *are* adapted to a centric, single axis hinge[:]; *and*
Figure 2:
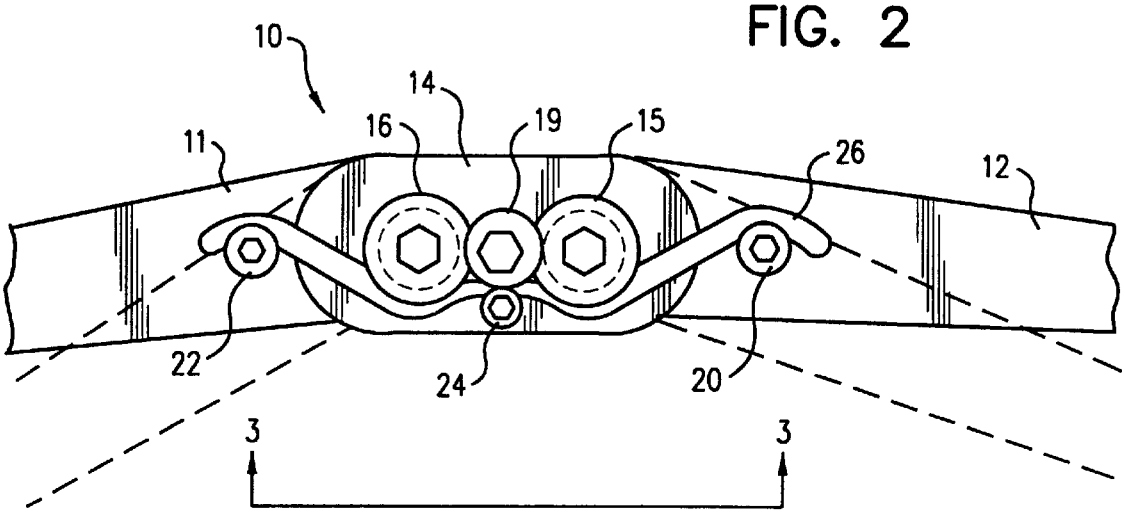
FIG. 2 is a front elevation view taken on line 2—2 of FIG. 1[:]*;*
Figure 3:
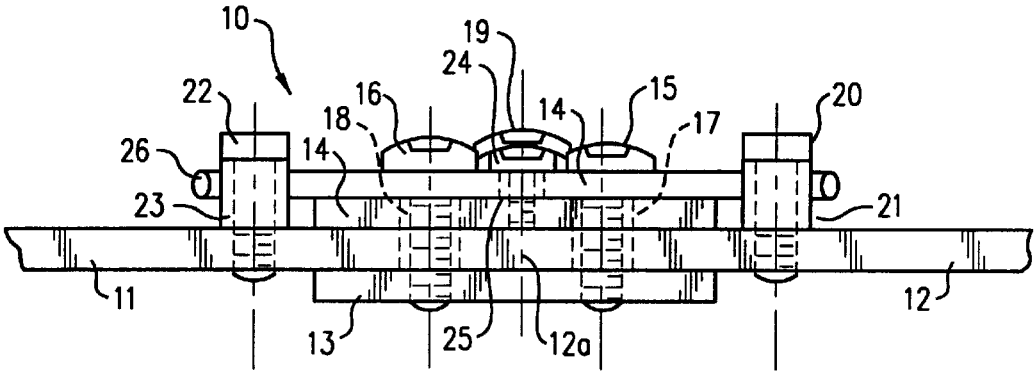
FIG. 3 is a side elevation view taken on line 3—3 of FIG. 2[:]
Figure 5:
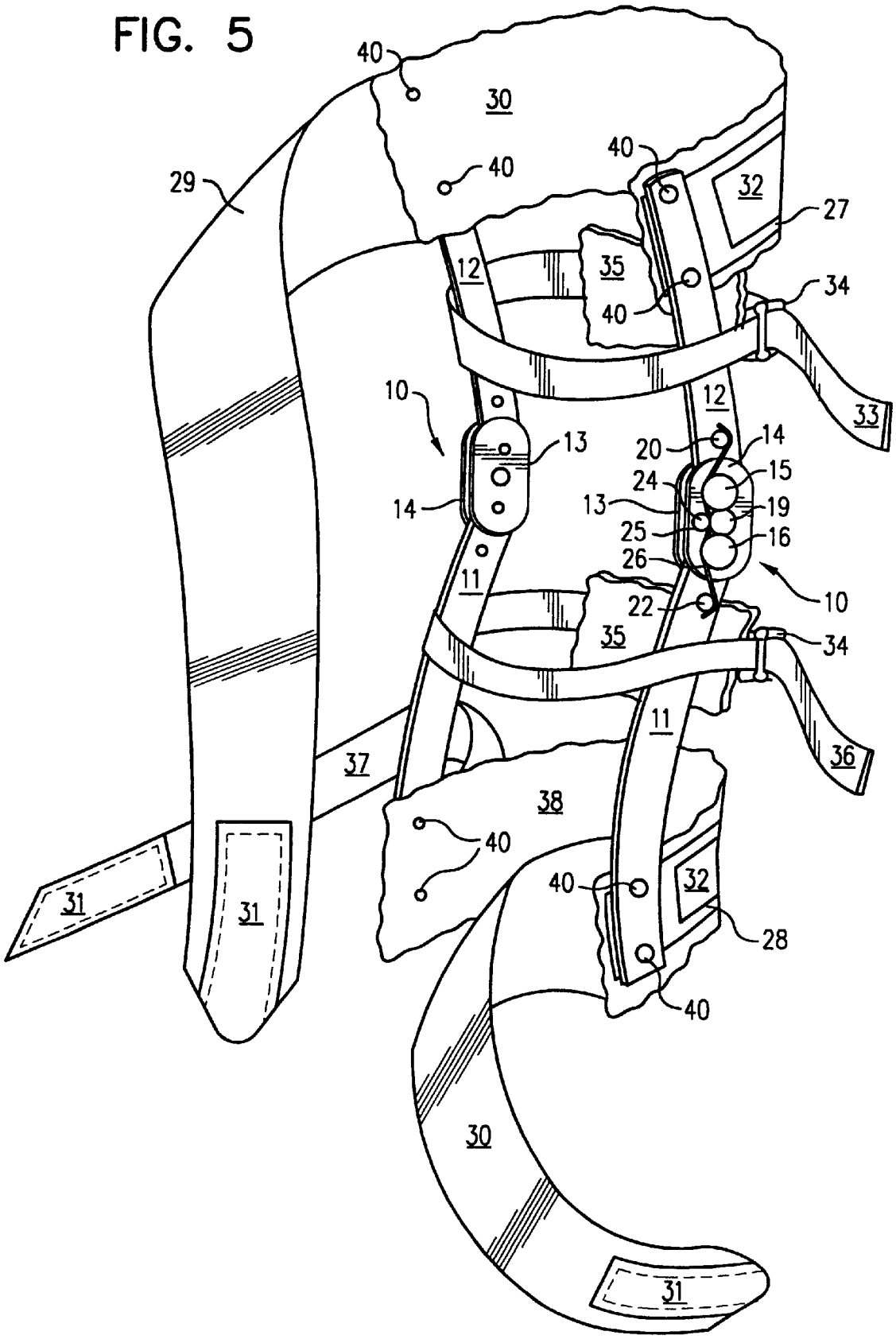
FIG. 5 is a complete overview of the [Extension Deceleration Orthosis labeling] *extension deceleration orthosis showing* individual components of the orthosis.

An orthotic fulcrum 10 according to principles of this [orthosis] *invention* includes an elongated, rigid, thin, flat lower bar 11 and an elongated, rigid, thin, flat upper bar 12. The bars are also called arms in the art. These arms, which should be of equal thickness, lie in the same plane and engage each other adjacently by means of gear teeth on each of their ends *at 12a* (*see FIG. 3*) in the polycentric orthotic fulcrum design. The polycentric orthotic fulcrum is known in the art. The arms are connected by rigid, inner plate 13 on the inside of the orthotic fulcrum and rigid, outer plate 14 on the outside of the orthotic fulcrum point so as to overlap the [arms] *arms'* engaged gear teeth. The arms and plates are fastened together by screws 15 and 16. These screws pass thru fulcrm point bushings 17 and 18 and fit into threaded holes in inner plate 13.

The orthotic fulcrum bushings 17 and 18 serve as pivot points for the orthotic fulcrum assembly. The length of hinge bushings 17 and 18 should be slightly shorter than the combined thickness of either arm plus the outer plate 14, since such design permits locking of the orthotic fulcrum in any position to facilitate manufacture, assembly and fitting into a large assembly, such as, an orthosis. When assembled for use the screws 15 and 16 are adjusted so as to permit the fulcrum point 10 to move freely over its range of motion, and then lock screw 19, which is positioned to simultaneously clamp a shoulder on each of screws 15 and 16, is tightened into a threaded hole in outer plate 14 so as to prevent screws 15 and 16 from turning.

Stops are provided on the geared ends of arms 11 and 12 so as to limit their range of motion. In order to prevent hyperextension of the limb, which can be caused when the angularly moving arms strike the stops, a deceleration means is provided, which is the [principle] *principal* improvement in the art, as described below.

Post 20 passes through friction reduction roller 21 and into a [variabley] *variably* placed threaded hole in the upper arm 12, to which it is tightened and adjusted so as to allow the roller 21 to turn freely. Post 22 passes through friction reduction roller 23 and into a variably placed hole in lower arm 11, to which it is tightened and adjusted so as to allow the roller 23 to turn freely. Pivot screw 24 passes through friction reduction roller 25 and is tightened into a threaded hole in outer plate 14, which hole is centered between assembled screws 15 and 16 on a line tangential to the adjacent pitch diameters of the gears on the ends of the assembled arms 11 and 12. A spring steel wire is formed serpentinely to make spring rod 26, which is assembled to fit around pivot screw 24 and roller 25. A shoulder on pivot screw 24 acts as a retainer to hold spring rod 26 against outer plate 14 and against the edges of screws 15 and 16. Spring rod 26 is curved to fit around screws 15 and 16 and is curved conversely to fit around friction reduction roller posts 20 and 22. The ends of spring rod 26 contact rollers 21 and 23 during extension of the orthotic fulcrum, resulting in deceleration of the angular velocity of the orthotic fulcrum and parts. The material and cross-sectional area of spring rod 26 can be varied to suit differences in the user's activity level and state of health and to suit required rates of deceleration of the angular motion of the hinge. The angle of curvature of spring rod 26 can be varied to adjust the point when deceleration occurs, which is a function of when rollers 21 and 23 first contact spring rod *26* during orthotic extension.

Upright arms 12 are attached to each other by means of a thin metal band 27, varying in thickness, width and length, each determined by requirements of individual appendage size, usually one-half the circumference of the appendage at the same length proximal to the fulcrum point. The means of fastening is rivets 40 drilled and pinned through both *arm* 12 and *band* 27. Band 28 is fastened to medial and laterial lower arms 11 in the same method as band 27 *is fastened to the upper arms 12*. Together with the arms 11 and 12, *bands* 27 and 28 make up the skeletal structure of the orthosis. Proximal circumference strap 29 encapsulates the appendage to the orthosis along with the distal circumference strap 30. These straps are compressive and hold the appendage firmly inside the orthosis. This is achieved by fastening *strap* 29 to *a band* 27 at one end by permanent fixation to interface or pad 39 and removable fastener 31 to *fixed fastener* 32 at the other end for circumferential wrap. The same is true for the attachment of *strap* 30 to *band* 28.

Two more prehension straps are used to encapsulate the appendage and they are the patella straps 33 and 36. *Strap* 33 is attached to *pad* 39 and *arm* 12 by nylon thread on one end and [34] *to* truss clip *34* on the other. *Truss clip* 34 is attached to *member* 35 with nylon thread in *a* reinforce stitch pattern completing the encapsulation of the knee, and also providing suspension. *Member* 35 is a pelite thermo pad that acts as an attachment point for *patella strap* 33 and *strap* 36. *Strap* 36 attaches to *pad* 38 in the same way *patella strap* 33 attaches to *pad* 39. [37 strap] *Strap 37* is *an* anti-rotation strap and runs up through the orthosis and around the medial or lateral or both sides of the knee in a spiraling wrap attaching to the [27] band *27* with *the* origin of the [28] band [, this] *28. This* resists rotary forces at the fulcrum point of the orthosis when applied to *a* flexing and extending appendage.

Although this invention has been described in the context of an orthotic device, it should be understood that [is] *it* also has application to any orthotic fulcrum contrivance, such as *an* orthotic power assisted arm, where it is desirable to decelerate the angular momentum of the orthotics fulcrum motion before a stop is contacted or before any restraining devices are excessively stretched.

We claim:

[1. An anatomical brace for applying a force for resisting extension having a hinge comprising:

a. a pair of elongated arms, of equal thickness, with geared ends engaging each other adjacently, said geared ends provided with stopping means to limit the range of motion of the arms on extension, said arms connected by inner and outer plates, said plates overlapping the geared ends, said plates and arms fastened together by at least one screw, said at least one screw passing through busings, which act as hinge pivot points, b. a lock screw which simultaneously clamps both the said plate fastening screws into position so as to permit free extension and flexion of the hinge, the improvement comprising:

c. a lightweight spring rod, which is assembled to said outer plate with a pivot screw, said pivot screw having a shoulder, said shoulder clamping the spring rod to the plate, with said spring rod serpentinely engaging on one side said pivot screw, and engaging on said rod's opposite side said at least one fastening screw, d. said pivot screw being assembled to the outer plate on a line tangential to the pitch diameter of the geared elongated arm ends by passing through first roller means which serve as a pivot center for the spring rod, e. means for controlling the application of said force for resisting extension comprising a friction reducing roller post selectively positioned on each arm, each of said posts being engaged by said spring rod on said one side as the arms are extended so that said spring rod biases the post toward flexion and therefore the arms toward flexion until the arms are in a preselected flexed positioned wherein further bending of the arms results in no force being applied by the rod against the posts;

f. the said friction reduction roller posts each comprising a screw fastened to the said elongated arm and a bushing through which said screw passes and which serves as second roller means to reduce friction when engaged by the spring rod during extension and flexion.]

*2. In an anatomical brace for applying a force for resisting extension having a hinge comprising:*

*a. a pair of elongated arms, of equal thickness, with geared ends engaging each other adjacently, said geared ends being provided with stopping means to limit the range of motion of the arms on extension, said arms being connected by inner and outer plates, said plates overlapping the geared ends, said plates and said arms being fastened together by at least one screw, said at least one screw passing through bushings, which act as hinge pivot points, and*

*b. a lock screw which simultaneously clamps both the said plate fastening screws into position so as to permit free extension and flexion of the hinge, the improvement comprising:*

*c. a lightweight spring road, which is assembled to said outer plate with a pivot screw, said pivot screw having a shoulder, said shoulder clamping the spring rod to the plate, with said spring rod serpentinely engaging on one side said pivot screw, and engaging on said rod's opposite side said at least one fastening screw,*

*d. said pivot screw being assembled to the outer plate on a line tangential to the pitch diameter of the geared elongated arm ends by passing through first roller means which serves as a pivot center for the spring rod,*

*e. means for controlling the application of said force for resisting extension comprising a friction reduction roller post selectively positioned on each arm, each of said posts being engaged by said spring rod on said one side as the arms are extended so that said spring rod biases the post toward flexion and therefore the arms toward flexion until the arms are in a preselected flexed position wherein further bending of the arms results in no force being applied by the rod against the posts, and*

*f. the said friction reduction roller posts each comprising a screw fastened to the said elongated arm and a bushing through which said screw passes and which serves as a second roller means to reduce friction when engaged by the spring rod during extension and flexion.*

*3. An orthotic device for providing extension stability and limiting hyperextension while providing flexion mobility, said device including:*

*a. an array of elongated, first and second arms;*

*b. means for attaching said arms to the body of a user on opposite sides of a joint that is to be protected by the device;*

*c. connector means at the apposite ends of said arms which connect said arms together for relative angular movement limited to a plane common to said arms; and*

*d. motion decelerating means for reducing the relative rate of movement between said arms, said decelerating means including; an elongated, energy-absorbing member capable of generating a reactive force that is proportional to the displacement of one end of the member relative to the other, means at a point intermediate the ends of the elongated member for fixing said member against movement relative to said connector means, and first and second stop means so located on said first and second arms as to be engageable only at particular times by opposite ends of said elongated member, said stop means being so relatively located and said elongated member being so contoured that both of said stop means are engageable by said elongated member only with the relative angle between said arms approaching a maximum, whereby: (a) said deceleration means remains inoperative and said arms can angularly move freely relative to each other as long as the relative angular displacement of said arms remains small enough that said elongated member does not simultaneously engage both of said stop means, but (b) both of said stop means will be engaged and the relative rate of angular movement between said arms increasingly reduced as the angular displacement between said arms is thereafter increased.*

*4. An orthotic device as defined in claim 3 wherein:*

*a. said connector means includes meshing gear means on the apposite ends of said arms, connector members so disposed on opposite sides of the array of arms as to prevent relative sideways movement of said arms, and members which extend through and span said connector members near the apposite ends of said arms to couple together said members and said arms and to provide shafts about which said arms can rotate; and*

*b. said decelerating means also includes means fixing said elongated member at approximately its midpoint and as aforesaid to one of said connector members.*

*5. An orthotic device as defined in claim 4 wherein:*

*a. the connector means comprises a headed member with a head that is engageable with said shaft providing members to prevent rotation of said shaft providing members;*

*b. said elongated member is trapped against one of said connector members by said headed member; and*

*c. the means for fixing said elongated member to said one of said connector members comprises a second headed member also confining said elongated member against said one of said connector members, said second headed member being so located on the opposite side of the elongated member from the first headed member as to trap the elongated member against the first headed member.*

*6. An orthotic device as defined in claim 4 which includes bushings supported from said one of said connector members and engageable by said elongated member to increase the resistance to relative angular movement of the arms afforded by said elongated member.*

*7. An orthotic device as defined in claim 6 in which the shaft-providing members extend through said bushings and fix said bushings to said one of said connector members.*

*8. An orthotic device as defined in claim 5 in which said shaft-providing members are threaded into a second of said connector members whereby, with said members locked against rotation, said one of and said second connector members can move apart to an extent which is sufficient to prevent said one of and said second members from frictionally restricting the relative rotation of said arms.*

*9. An orthotic device as defined in claim 5 in which:*

*a. said first threaded member is located along a line extending between the axes of elongation of the shaft-providing members and approximately midway between said axes; and*

*b. the second threaded member is located along a second line extending normally to the first-mentioned line and passing through the axis of elongation of the first headed member.*

*10. An orthotic device as defined in claim 4 in which:*

*a. the apposite end portions of said arms have parallel sides and are of equal thickness; and*

*b. said connector members are flat plates.*

*11. An orthotic device as defined in claim 3 in which said elongated member is fabricated of a resiliently deformable material and has a serpentine configuration.*

*12. An orthotic device as defined in claim 3 in which:*

*a. the end portions of the elongated member are trained around the stop means when they are engaged with said stop means as aforesaid; and*

*b. said stop means comprise rollers so engageable by said elongated element end portions as to minimize friction between said elongated member and said stop means and thereby provide for flexion mobility in said device.*

* * * * *